United States Patent [19]

Horovitz et al.

[11] Patent Number: 5,093,129
[45] Date of Patent: Mar. 3, 1992

[54] METHOD FOR TREATING ADDICTION TO A DRUG OF ABUSE EMPLOYING AN ACE INHIBITOR

[75] Inventors: Zola P. Horovitz, Princeton; Abraham Sudilovsky, Lawrenceville, both of N.J.

[73] Assignee: E. R. Squibb & Sons, Inc., Princeton, N.J.

[21] Appl. No.: 303,504

[22] Filed: Jan. 30, 1989

[51] Int. Cl.⁵ ............................................. A61K 9/48
[52] U.S. Cl. .................................. 424/451; 424/464
[58] Field of Search ....................... 514/18, 19, 646; 424/464

[56] References Cited

U.S. PATENT DOCUMENTS

| | | | |
|---|---|---|---|
| 4,046,889 | 9/1987 | Ondetti et al. | 424/244 |
| 4,316,906 | 2/1982 | Ondetti et al. | 424/274 |
| 4,337,201 | 6/1982 | Petrillo | 548/413 |
| 4,416,871 | 11/1983 | Walter et al. | 514/18 |
| 4,423,242 | 12/1983 | Wilkinson et al. | 560/41 |
| 4,452,790 | 6/1984 | Karanewsky et al. | 424/200 |
| 4,460,604 | 7/1984 | Lednicer | 514/646 |
| 4,652,641 | 3/1987 | Parsons | 540/523 |

FOREIGN PATENT DOCUMENTS

3610391 A1  3/1988  Fed. Rep. of Germany .
2607004    11/1986  France .

OTHER PUBLICATIONS

"Angiotensin Converting Enzyme Inhibitors: Animal Experiments Suggest a New Pharmacological Treatment for Alcohol Abuse in Humans," G. Spinosa et al., Alcoholism: Clinical and Experimental Research, vol. 12, No. 1, Jan./Feb., 1988, pp. 65–70.

S. J. Dolin et al., "Calcium Channel Antagonists Decrease the Ethanol Withdrawal Syndrome" British Journal of Pharm., vol. 87, Mar. suppl. 40P (1986).

Qin Wencai et al., "Nimodipine, Nifedipine and Vincamine Improve Amnesia Induced by Anisodine and Sodium Nitrite in Rats and Mice" Chung Kuo I Hsueh Ko Hsueh Yuan Hsueh Pao, Oct. 1986, 8(5), pp. 366–370.

Adler, L. et al., "Calcium Channel Antagonists in Tardive Dyskinesia and Psychosis," Dec. 1987 meeting of the Amer. College of Neuropsychopharmacology, San Juan, Puerto Rico.

Leys, D. et al. "Diltiazem for Tardive Dyskinesia," The Lancet, Jan. 30, 1988.

S. H. Croog et al., "The Effects of Antihypertensive Therapy on the Quality of Life" New Engl. J. of Med. 314:1657–1664 (6/26/86).

Primary Examiner—Thurman K. Page
Assistant Examiner—Leon R. Horne
Attorney, Agent, or Firm—Burton Rodney

[57] ABSTRACT

A method is provided for treating addiction to a drug of abuse such as nicotine, cocaine or diazepam, by inhibiting appetitie or desire for such drug by administering an ACE inhibitor, such as captopril, fosinopril, zofenopril or SQ 29,852, alone or in combination with a calcium channel blocker such as diltiazem or nifedipine, over a prolonged period of treatment.

20 Claims, No Drawings

METHOD FOR TREATING ADDICTION TO A DRUG OF ABUSE EMPLOYING AN ACE INHIBITOR

FIELD OF THE INVENTION

The present invention relates to a method for treating addiction to a drug of abuse, such as nicotine, cocaine or diazepam, by administering an ACE inhibitor, such as captopril, SQ 29,852, zofenopril, fosinopril, enalapril or lisinopril, alone or in combination with a calcium channel blocker, such as diltiazem, nifedipine or verapamil.

BACKGROUND OF THE INVENTION

U.S. Pat. Nos. 4,046,889 and 4,105,776 to Ondetti et al discloses proline derivatives, including captopril, which are angiotensin converting enzyme (ACE) inhibitors useful for treating hypertension.

U.S. Pat. No. 4,337,201 to Petrillo discloses phosphinylalkanoyl substituted prolines, including fosinopril, which are ACE inhibitors useful for treating hypertension.

U.S. Pat. No. 4,374,829 discloses carboxyalkyl dipeptide derivatives, including enalapril, which are ACE inhibitors useful for treating hypertension.

U.S. Pat. No. 4,452,790 to Karanewsky et al. discloses phosphonate substituted amino or imino acids and salts thereof and covers (S)-1-[6-amino-2-[[hydroxy(4-phenylbutyl)-phosphinyl]-oxy]-1-oxohexyl]-L-proline (SQ 29,852). These compounds are ACE inhibitors useful in treating hypertension.

U.S. Pat. No. 4,316,960 to Ondetti et al. discloses ether and thioether mercaptoacyl prolines which are ACE inhibitors useful in treating hypertension.

This Ondetti et al patent covers zofenopril.

"Angiotensin Converting Enzyme Inhibitors: Animal Experiments Suggest a New Pharmacological Treatment for Alcohol Abuse in Humans", G. Spinosa et al., Alcoholism: Clinical and Experimental Research, Vol. 12, No. 1, January/February, 1988, Pages 65-70 discloses that angiotensin converting enzyme inhibitors significantly and specifically reduce voluntary alcohol intake in rats.

Dolin, S. J., et al., "Calcium Channel Antagonists Decrease the Ethanol Withdrawal Syndrome," British Journal of Pharmacology, Vol. 87, Mar. Suppl. 40P, 1986 discloses that nitrendipine and verapamil significantly decreased the incidence of the convulsive component of the ethanol withdrawal syndrome and nitrendipine and flunarizine significantly decreased the mortality of rats treated.

DESCRIPTION OF THE INVENTION

In accordance with the present invention, a method is provided for treating addiction to a drug of abuse in mammalian species wherein an antiaddictive effective amount of an angiotensin converting enzyme (ACE) inhibitor alone or in combination with a calcium channel blocker is systemically, such as orally or parenterally, administered.

It is theorized that a patient treated with an angiotensin-converting enzyme inhibitor, in accordance with the present inveniton, will have a reduced appetite or desire for the drug of addiction and will therefore voluntarily reduce his consumption of the drug. In this manner, the patients need for the drug and thus his addiction to the drug will be diminished.

The term "drugs of abuse" as used herein refer to nicotine (for example, from smoking cigarettes), cocaine, diazepam, other benzodiazepines, amphetamines, morphine, heroin, marihuana and the like, but does not include alcohol.

Where a combination of ACE inhibitor and calcium channel blocker are to be used, the ACE inhibitor will be employed in a weight ratio to the calcium channel blocker of within the range of from about 0.1:1 to about 10:1 and preferably from about 0.4:1 to about 2.5:1.

The angiotensin converting enzyme inhibitor which may be employed herein includes substituted proline derivatives, such as any of those disclosed in U.S. Pat. Nos. 4,046,889 or 4,105,776 to Ondetti et al mentioned above, with captopril, that is, 1-[(2S)-3-mercapto-2-methylpropionyl]-L-proline, being preferred, carboxyalkyl dipeptide derivatives, such as any of those disclosed in U.S. Pat. No. 4,374,829 mentioned above, with N-(1-ethoxycarbonyl-3-phenylpropyl)-L-alanyl-L-proline, that is, enalapril, being preferred.

Other examples of angiotensin converting enzyme inhibitors suitable for use herein include any of the phosphonate substituted amino or imino acids or salts disclosed in U.S. Pat. No. 4,452,790 with (S)-1-[6-amino-2-[[hydroxy-(4-phenylbutyl)phosphinyl]oxy]-1-oxohexyl]-L-proline (SQ 29,852) being preferred, phosphinylalkanoyl prolines disclosed in U.S. Pat. No. 4,168,267 mentioned above with fosinopril being preferred, mercaptoacyl derivatives of substituted prolines, disclosed in U.S. Pat. No. 4,316,906 with zofenopril being preferred, any of the phosphinylalkanoyl substituted prolines disclosed in U.S. Pat. No. 4,337,201 discussed above, and the phosphonamidates disclosed in U.S. Pat. No. 4,432,971 discussed above.

Other examples of ACE inhibitors that may be employed herein include Beecham's BRL 36,378 as disclosed in European patent Nos. 80822 and 60668; Chugai's MC-838 disclosed in CA. 102:72588v and Jap. J. Pharmacol. 40:373 (1986); Ciba-Geigy's CGS 14824 (3-([1-ethoxycarbonyl-3-phenyl-(1S)-propyl]amino)-2,3,4,5-tetrahydro-2-oxo-1-(3S)-benzazepine-1 acetic acid HCl), disclosed in U.K. Patent No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res. 39:671 (1986); 40:543 (1986); ramipril (Hoechst) disclosed in Eur. Patent No. 79-022 and Curr. Ther. Res. 40:74 (1986); Ru 44570 (Hoechst) disclosed in Arzneimittelforschung 35:1254 (1985), cilazapril (Hoffman-LaRoche) disclosed in J. Cardiovasc. Pharmacol. 9:39 (1987); R$_o$ 31-2201 (Hoffman-LaRoche) disclosed in FEBS Lett. 165:201 (1984); lisinopril (Merck) disclosed in Curr. Therap. Res. 37:342 (1985) and Eur. patent appl. No. 12-401, indalapril (delapril) disclosed in U.S. Pat. No. 4,385,051; rentiapril (fentiapril, Santen) disclosed in Clin. Exp. Pharmacol. Physiol. 10:131 (1983); indolapril (Schering) disclosed in J. Cardiovasc. Pharmacol. 5:643, 655 (1983); spirapril (Schering) disclosed in Acta. Pharmacol. Toxicol. 59 (Supp. 5):173 (1986); perindopril (Servier) disclosed in Eur. J. Clin. Pharmacol. 31:519 (1987); quinapril (Warner-Lambert) disclosed in U.S. Pat. No. 4,344,949 and CI 925 (Warner-Lambert) ([3S-[2[R(*)R(*)]]3R(*)]-2-[2-[[1-(ethoxycarbonyl)-3-phenylpropyl]amino[-1-oxopropyl]-1,2,3,4-tetrahydro-6,7-dimethoxy-3-isoquinolinecarboxylic acid HCl) disclosed in Pharmacologist 26:243, 266 (1984), WY-44221 (Wyeth) disclosed in J. Med. Chem. 26:394 (1983).

Preferred are those ACE inhibitors which are proline or substituted proline derivatives.

The above-mentioned U.S. patents are incorporated herein by reference.

The calcium antagonist which will be used herein may be diltiazem which is disclosed in U.S. Pat. No. 3,562,257 and which has the chemical name 3-(acetyloxy)-5-[2-(dimethylamino)ethyl-2,3-dihydro-2-(4-methoxyphenyl)-1,5-benzothiazepin-4(5H)-one and the structure

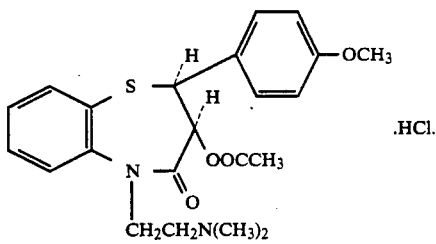

4-Phenyl-1,4-dihydropyridine calcium antagonists may be employed which will have the structure

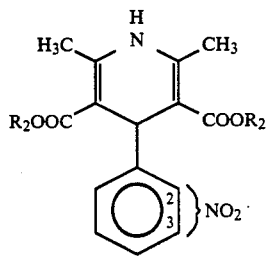

wherein $R_1$ and $R_2$ may be the same or different and are lower alkyl or lower alkoxy (lower alkyl) where lower alkyl and lower alkoxy contain 1 to 4 carbons.

The above compounds and methods for preparing same are disclosed in U.S. Pat. Nos. 3,644,627, 3,485,847, 3,488,359, 3,574,843, 3,799,934, 3,932,645 and 4,154,839 which are incorporated herein by reference.

The dihydropyridine calcium antagonist present in the composition of the invention will preferably be nifedipine, that is, the compound of formula C wherein $R_1$ is $CH_3$, $R_2$ is $CH_3$ and $NO_2$ is at the 2-position, namely,

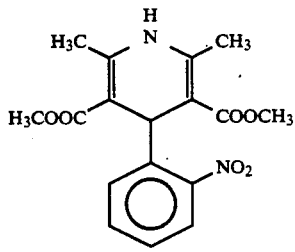

which is disclosed in U.S. Pat. Nos. 3,644,627 and 3,485,847.

Other preferred 4-phenyl-1,4-dihydropyridine calcium antagonists suitable for use herein include niludipine, that is, the compound of formula C wherein $R_1$ is $-(CH_2)_2OC_3H_7$, $R_2$ is $-(CH_2)_2OC_3H_7$ and $NO_2$ is at the 3-position (disclosed in U.S. Pat. Nos. 3,488,359 and 3,574,843); nimodipine, that is the compound of formula C wherein $R_1$ is $-(CH_2)_2OCH_3$, $R_2$ is $-CH(CH_3)_2$ and $NO_2$ is at the 3-position (disclosed in U.S. Pat. Nos. 3,799,934 and 3,932,645); nitrendipine, that is, the compound of formula C wherein $R_1$ is $-CH_2CH_3$, $R_2$ is $-CH_3$ and $NO_2$ is at the 3-position (disclosed in U.S. Pat. Nos. 3,799,934 and 3,932,645); and nisoldipine, that is, the compound of formula C wherein $R_1$ is $-CH_3$, $R_2$ is $-CH_2CH(CH_3)_2$ and $NO_2$ is at the 2-position (disclosed in U.S. Pat. Nos. 3,799,934, 3,932,645 and 4,154,839). Verapamil may also be employed.

In addition, verapamil may be employed.

The disclosure of the above-mentioned patents and references are incorporated herein by reference.

In carrying out the method of the present invention, the angiotensin converting enzyme inhibitor alone or in combination with the calcium channel blocker may be administered to mammalian species, such as monkeys, dogs, cats, rats and humans, and as such may be incorporated in a conventional systemic dosage form, such as a tablet, capsule, elixir or injectable. The above dosage forms will also include the necessary carrier material, excipient, lubricant, buffer, antibacterial, bulking agent (such as mannitol), anti-oxidants (ascorbic acid of sodium bisulfite) or the like. Oral dosage forms are preferred, although parenteral forms such as intramuscular, intraperitoneal, or intravenous are quite satisfactory as well.

The dose administered must be carefully adjusted according to age, weight and condition of the patient, as well as the route of administration, dosage form and regimen and the desired result.

Thus, for oral administration, a satisfactory result may be obtained employing the ACE inhibitor in an amount within the range of from about 0.01 mg/kg to about 100 mg/kg and preferably from about 0.1 mg/kg to about 25 mg/kg alone or in combination with the calcium channel blocker in an amount within the range of from about 0.01 mg/kg to about 100 mg/kg and preferably from about 0.1 mg/kg to about 25 mg/kg with the ACE inhibitor and calcium channel blocker being employed together in the same oral dosage form or in separate oral dosage forms taken at the same time.

A preferred oral dosage form, such as tablets or capsules, will contain the ACE inhibitor in an amount of from about 0.1 to about 500 mg, preferably from about 5 to about 200 mg, and more preferably from about 25 to about 150 mg, alone or with the calcium channel blocker in an amount of from about 1 to about 350 mg, preferably from about 2 to about 200 mg, and more preferably from about 30 to about 150 mg.

For parenteral administration, the ACE inhibitor will be employed in an amount within the range of from about 0.005 mg/kg to about 10 mg/kg and preferably from about 0.01 mg/kg to about 1 mg/kg, alone or with the calcium channel blocker in an amount within the range of from about 0.005 mg/kg to about 20 mg/kg and preferably from about 0.01 mg/kg to about 2 mg/kg.

The composition described above may be administered in the dosage forms as described above in single or divided doses of one to four times daily. It may be advisable to start a patient on a low dose combination and work up gradually to a high dose combination.

Tablets of various sizes can be prepared, e.g., of about 50 to 700 mg in total weight, containing one or both of the active substances in the ranges described above, with the remainder being a physiologically acceptable carrier of other materials according to accepted pharmaceutical practice. These tablets can, of course, be scored to provide for fractional doses. Gelatin capsules can be similarly formulated.

Liquid formulations can also be prepared by dissolving or suspending one or the combination of active substances in a conventional liquid vehicle acceptable for pharmaceutical administration so as to provide the desired dosage in one to four teaspoonfuls.

Such dosage forms can be administered to the patient on a regimen of one to four doses per day.

According to another modification, in order to more finely regulate the dosage schedule, the active substances may be administered separately in individual dosage units at the same time or carefully coordinated times. Since blood levels are built up and maintained by a regulated schedule of administration, the same result is achieved by the simultaneous presence of the two substances. The respective substances can be individually formulated in separate unit dosage forms in a manner similar to that described above.

Fixed combinations of ACE inhibitor and calcium channel blocker are more convenient and are preferred, especially in tablet or capsule form for oral administration.

In formulating the compositions, the active substances, in the amounts described above, are compounded according to accepted pharmaceutical practice with a physiologically acceptable vehicle, carrier, excipient, binder, preservative, stabilizer, flavor, etc., in the particular type of unit dosage form.

Illustrative of the adjuvants which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the active compound, water, alcohol or the like as the carrier, glycerol as solubilizer, sucrose as sweetening agent, methyl and propyl parabens as preservatives, a dye and a flavoring such as cherry or orange.

Many of the active substances described above form commonly known, pharmaceutically acceptable salts such as alkali metal and other common basic salts or acid addition salts, etc. References to the base substances are therefore intended to include those common salts known to be substantially equivalent to the parent compound.

The formulations as described above will be administered for a prolonged period, that is, for as long as the potential for or desire for a drug of abuse remains. Sustained release forms of such formulations which may provide such amounts biweekly, weekly, monthly and the like may also be employed. A dosing period of at least one to two weeks are required to achieve minimal benefit.

The following Examples represent preferred embodiments of the present invention.

EXAMPLE 1

A captopril formulation suitable for oral administration in inhibiting desire or appetite for a drug of abuse such as diazepam is set out below.

1000 tablets each containing 100 mg of 1-[(2S)-3-mercapto-2-methylpropionyl]-L-proline were produced from the following ingredients.

| | |
|---|---|
| 1-[(2S)-3-Mercapto-2-methylpropionyl]-L-proline (captopril) | 100 g |
| Corn starch | 50 g |
| Gelatin | 7.5 g |
| Avicel (microcrystalline cellulose) | 25 g |
| Magnesium stearate | 2.5 g |

The captopril and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 100 mg of active ingredient which is used for inhibiting appetite or desire for a drug of abuse.

EXAMPLE 2

1000 tablets each containing 200 mg of captopril are produced from the following ingredients:

| | |
|---|---|
| Captopril | 200 g |
| Lactose | 100 g |
| Avicel | 150 g |
| Corn starch | 50 g |
| Magnesium stearate | 5 g |

The captopril, lactose and Avicel are admixed, then blended with the corn starch. Magnesium stearate is added. The dry mixture is compressed in a tablet press to form 1000 505 mg tablets each containing 200 mg of active ingredient. The tablets are coated with a solution of Methocel E 15 (methyl cellulose) including as a color a lake containing yellow #6. The resulting tablets are useful in inhibiting appetite or desire for a drug of abuse such as nicotine.

EXAMPLE 3

Two piece #1 gelatin capsules each containing 250 mg of captopril are filled with a mixture of the following ingredients:

| | |
|---|---|
| Captopril | 250 mg |
| Magnesium stearate | 7 mg |
| USP lactose | 193 mg |

The resulting capsules are useful in inhibiting appetite or desire for a drug of abuse such as cocaine.

EXAMPLE 4

An injectable solution for use in inhibiting appetite or desire for a drug of abuse such as an amphetamine is produced as follows:

| | |
|---|---|
| Captopril | 500 mg |
| Methyl paraben | 5 mg |
| Propyl paraben | 1 mg |
| Sodium chloride | 25 g |
| Water for injection qs. | 5 l. |

The captopril, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains 5 ml of solution in a concentration of 100 mg of active ingredient per ml of solution for injection.

EXAMPLE 5

Tablets for use in inhibiting appetite or desire for a drug of abuse such as morphine are prepared as described in Example 1 except that N-(1-ethoxycarbonyl-3-phenylpropyl)-L-alanyl-L-proline (enalapril) is used in place of captopril.

EXAMPLE 6

An injectable for use in inhibiting appetite or desire for a drug of abuse such as heroin is prepared as described in Example 4 except that N-(1-ethoxycarbonyl-3-phenylpropyl)-L-alanyl-L-proline (enalapril) is employed in place of captopril.

EXAMPLE 7

A zofenopril formulation suitable for oral administration in inhibiting appetite or desire for a drug of abuse such as marihuana is set out below.

1000 tablets each containing 100 mg of zofenopril are produced from the following ingredients.

| | |
|---|---|
| [1(S),4(S)]-1-[3-(benzoylthio)-2-methyl-1-oxopropyl-4-(phenylthio)-L-proline (zofenopril) | 100 g |
| Corn starch | 50 g |
| Gelatin | 7.5 g |
| Avicel (microcrystalline cellulose) | 25 g |
| Magnesium stearate | 2.5 g |

The zofenopril and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 100 mg of active ingredient which is used for inhibiting appetite or desire for a drug of abuse.

EXAMPLE 8

By substituting 100 g of fosinopril for the zofenopril in Example 7, 1000 tablets each containing 100 mg of the fosinopril are produced which is useful in inhibiting appetite or desire for a drug of abuse such as nicotine.

EXAMPLE 9

1000 tablets each containing 200 mg of fosinopril are produced from the following ingredients:

| | |
|---|---|
| Fosinopril | 200 g |
| Lactose | 100 g |
| Avicel | 150 g |
| Corn starch | 50 g |
| Magnesium stearate | 5 g |

The fosinopril, lactose and Avicel are admixed, then blended with the corn starch. Magnesium stearate is added. The dry mixture is compressed in a tablet press to form 1000 505 mg tablets each containing 200 mg of active ingredient. The tablets are coated with a solution of Methocel E 15 (methyl cellulose) including as a color a lake containing yellow #6. The resulting tablets are useful in inhibiting appetite or desire for a drug of abuse such as diazepam.

EXAMPLE 10

Tablets for use in inhibiting appetite or desire for a drug of abuse such as nicotine are prepared as described in Example 1 except that 1-[N-[hydroxy(4-phenylbutyl)phosphinyl]-L-alanyl-L-proline, disodium salt (prepared as described in U.S. Pat. No. 4,432,971) is used in place of captopril.

EXAMPLE 11

An injectable for use in inhibiting appetite or desire for a drug of abuse such as nicotine is prepared as described in Example 4 except that 1-[N-[hydroxy(4-phenylbutyl)phosphinyl]-L-alanyl-L-proline, disodium salt (prepared as described in U.S. Pat. No. 4,432,971) is used in place of captopril.

EXAMPLE 12

A captopril-diltiazem formulation suitable for oral administration in inhibiting appetite or desire for a drug of abuse such as diazepam is set out below.

1000 tablets each containing 100 mg of 1-[(2S)-3-mercapto-2-methylpropionyl]-L-proline and 100 mg of diltiazem are produced from the following ingredients:

| | |
|---|---|
| 1-(2S)-3-mercapto-2-methylpropionyl]-L-proline (captopril) | 100 g |
| Diltiazem | 100 g |
| Corn starch | 50 g |
| Gelatin | 7.5 g |
| Avicel (microcrystalline cellulose) | 25 g |
| Magnesium stearate | 2.5 g |

The captopril, diltiazem and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 200 mg of active ingredients which is used for inhibiting appetite or desire for a drug of abuse.

EXAMPLE 13

1000 tablets each containing 200 mg of captopril and 200 mg nifedipine are produced from the following ingredients:

| | |
|---|---|
| Captopril | 200 g |
| Nifedipine | 200 g |
| Lactose | 100 g |
| Avicel | 150 g |
| Corn starch | 50 g |
| Magnesium stearate | 5 g |

The captopril, nifedipine, lactose and Avicel are admixed, then blended with the corn starch. Magnesium stearate is added. The dry mixture is compressed in a tablet press to form 1000 505 mg tablets each containing 200 mg of each active ingredient. The tablets are coated with a solution of Methocel E 15 (methyl cellulose) including as a color a lake containing yellow #6. The resulting tablets are useful in inhibiting appetite or desire for a drug of abuse such as nicotine.

EXAMPLE 14

Two piece #1 gelatin capsules each containing 250 mg of enalapril and 150 mg of nitrendipine are filled with a mixture of the following ingredients:

| | |
|---|---|
| Enalapril | 250 mg |
| Nitrendipine | 150 mg |
| Magnesium stearate | 7 mg |
| USP lactose | 193 mg |

The resulting capsules are useful in inhibiting appetite or desire for a drug of abuse such as cocaine.

EXAMPLE 15

An injectable solution for use in inhibiting appetite or desire for a drug of abuse such as morphine is produced as follows:

| | |
|---|---|
| Captopril | 500 mg |
| Diltiazem | 300 mg |
| Methyl paraben | 5 g |
| Propyl paraben | 1 g |
| Sodium chloride | 25 g |
| Water for injection qs. | 5 L. |

The captopril, diltiazem, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains 5 ml of solution in a concentration of 100 mg of active ingredient per ml of solution for injection.

EXAMPLE 16

Tablets for use in inhibiting appetite or desire for a drug of abuse such as heroin are prepared as described in Example 12 except that N-(1-ethoxycarbonyl-3-phenylpropyl)-L-alanyl-L-proline (enalapril) is used in place of captopril and nifedipine is used in place of diltiazem.

EXAMPLE 17

Tablets for use in inhibiting appetite or desire for a drug of abuse are prepared following the procedure of Example 12 except that zofenopril is employed in place of captopril and nisoldipine is used in place of diltiazem.

EXAMPLE 18

Tablets for use in inhibiting appetite or desire for a drug of abuse are prepared following the procedure of Example 12 except that fosinopril is employed in place of captopril.

EXAMPLE 19

Tablets for use in inhibiting appetite or desire for a drug of abuse are prepared following the procedure of Example 12 except that alacepril is employed in place of captopril.

EXAMPLE 20

Tablets for use in inhibiting appetite or desire for a drug of abuse are prepared following the procedure of Example 13 except that (S)-1-[6-amino-2-[[hydroxy-(4-phenylbutyl)phosphinyl]oxy]-1-oxohexyl]-L-proline or lisinopril is employed in place of captopril.

What is claimed is:

1. A method for treating addiction to a drug of abuse in a mammalian specie, which comprises administering to a mammalian specie in need of such treatment an antiaddictive effective amount of an angiotensin converting enzyme inhibitor selected from the group consisting of catopril, (S)-1-[6-amino-2-[[hydroxy(4-phenylbutyl) phosphinoyl]oxy]-1-oxohexyl]-L-proline, fosinopril, zofenopril enalapril and lisinopril alone or in combination with a calcium channel blocker wherein said inhibitor is administered in single or divided doses of from about 0.1 to about 500 mg/ one to four time daily and the calcium channel blocker is administered in single or divided doses of from about 1 to about 300 mg/1 to 4 times daily.

2. The method as defined in claim 1 wherein the angiotensin converting enzyme inhibitor is a phosphonate substituted amino or imino acid or salt thereof, a proline derivative, a substituted proline derivative, a carboxyalkyl dipeptide derivative, a phosphinylalkanoyl proline derivative or a phosphonamidate derivative.

3. The method as defined in claim 1 wherein said angiotensin converting enzyme inhibitor is a proline derivative or a substituted proline derivative.

4. The method as defined in claim 1 wherein said angiotensin converting enzyme inhibitor is a carboxyalkyl dipeptide derivative.

5. The method as defined in claim 1 wherein said angiotensin converting enzyme inhibitor is a phosphinylalkanoyl proline derivative, a phosphoramidate derivative, or a phosphonate substituted amino or imino acid or salt thereof.

6. The method as defined in claim 1 wherein said angiotensin converting enzyme inhibitor is captopril.

7. The method as defined in claim 1 wherein said angiotensin converting enzyme inhibitor is enalapril.

8. The method as defined in claim 1 wherein said angiotensin converting enzyme inhibitor is lisinopril.

9. The method as defined in claim 1 wherein said angiotensin converting enzyme inhibitor is zofenopril.

10. The method as defined in claim 1 wherein said angiotensin converting enzyme inhibitor is fosinopril.

11. The method as defined in claim 1 wherein said angiotensin converting enzyme inhibitor is (S)-1-[6-amino-2-[[hydroxy(4-phenylbutyl)phosphinyl]oxy]-1-oxohexyl]-L-proline.

12. The method as defined in claim 1 wherein the angiotensin converting enzyme inhibitor is administered with a calcium channel blocker.

13. The method as defined in claim 12 wherein the calcium channel blocker is diltiazem, a 4-phenyl-1,4-dihydropyridine or verapamil.

14. The method as defined in claim 13 wherein the 4-phenyl-1,4-dihydropyridine is nifedipine or nitrendipine.

15. The method as defined in claim 12 wherein the angiotensin converting enzyme inhibitor is employed in a weight ratio to the calcium channel blocker of within the range of from about 0.1:1 to about 10:1.

16. The method as defined in claim 1 wherein the drug of abuse is nicotine, cocaine, diazepam, an amphetamine, morphine, heroin or marihuana.

17. A method for inhibiting appetite or desire for nicotine, in a mammalian specie, which comprises administering to a mammalian specie in need of such treatment an antiadditive effective amount of an angiotensin converting enzyme inhibitor in combination with calcium channel blocker.

18. A method for inhibiting appetite or desire for heroin, cocaine, morphine or marihuana in a mammalian specie, which comprises administering to a mammalian specie in need of such treatment an antiadditive effective amount of an angiotensin converting enzyme inhibitor in combination with a calcium channel blocker.

19. The method as defined in claim 18 wherein the angiotensin converting enzyme inhibitor administered is SQ 29,852, captopril, fosinopril, zofenopril, enalapril or lisinopril.

20. A method for inhibiting appetite or desire for diazepam or other benzodiazepine or an amphetamine in a mammalian specie, which comprises administering to a mammalian specie in need of such treatment an antiadditive effective amount of an angiotensin converting enzyme inhibitor in combination with a calcium channel blocker.

* * * * *